United States Patent [19]

Farnholtz

[11] Patent Number: 5,895,391
[45] Date of Patent: Apr. 20, 1999

[54] BALL LOCK JOINT AND INTRODUCER FOR VASO-OCCLUSIVE MEMBER

[75] Inventor: Roger Farnholtz, Fremont, Calif.

[73] Assignee: Target Therapeutics, Inc., Freemont, Calif.

[21] Appl. No.: 08/714,932

[22] Filed: Sep. 27, 1996

[51] Int. Cl.⁶ ................................................ A61F 11/00
[52] U.S. Cl. ................................ 606/108; 606/200
[58] Field of Search ................................ 606/200, 108, 606/127, 195, 198, 191; 604/264

[56] References Cited

U.S. PATENT DOCUMENTS

| | | |
|---|---|---|
| 4,739,768 | 4/1988 | Engelson . |
| 4,813,934 | 3/1989 | Engelson et al. . |
| 4,884,579 | 12/1989 | Engelson . |
| 4,913,141 | 4/1990 | Hillstead ................... 606/108 |
| 4,994,069 | 2/1991 | Ritchart et al. . |
| 5,098,374 | 3/1992 | Othel-Jacobsen et al. ............ 606/108 |
| 5,108,407 | 4/1992 | Geremia et al. . |
| 5,122,136 | 6/1992 | Guglielmi et al. . |
| 5,234,437 | 8/1993 | Sepetka . |
| 5,250,071 | 10/1993 | Palermo ...................... 606/198 |
| 5,261,916 | 11/1993 | Engelson . |
| 5,263,964 | 11/1993 | Purdy . |
| 5,304,195 | 4/1994 | Twyford, Jr. et al. ............. 606/191 |
| 5,350,397 | 9/1994 | Palermo et al. ............... 606/191 |
| 5,354,295 | 10/1994 | Guglielmi et al. . |
| 5,417,708 | 5/1995 | Hall et al. . |
| 5,476,505 | 12/1995 | Limon ........................... 606/191 |
| 5,538,504 | 7/1996 | Linden et al. ............... 604/264 |

FOREIGN PATENT DOCUMENTS

| | | |
|---|---|---|
| 9413645 | 10/1994 | Germany . |
| 92/21400 | 12/1992 | WIPO . |
| 93/11719 | 6/1993 | WIPO . |

*Primary Examiner*—Robert A. Hafer
*Assistant Examiner*—Justine R. Yu
*Attorney, Agent, or Firm*—Morrison & Foerster L.L.P.

[57] ABSTRACT

This is an assembly for controllably delivering vaso-occlusive devices to a selected site within the vasculature or other lumen of the human body by the use of a catheter. In particular, the device includes a holding member which is at least generally tubular and has an opening through the tubular wall. The vaso-occlusive device to be delivered has on one end a mating member which may be at least partially pressed into the opening in the wall of the holding member. The mating member attached to the vaso-occlusive member is held in the opening with an interference wire. The interference wire is axially movable within the holding member and has a diameter sufficient to hold the mating member within the wall opening. Upon proximal movement of the interference wire, the mating member becomes free to leave the holding member. The interference wire may be tapered or not. The vaso-occlusive member may be a helically wound coil or a braid or other appropriate form.

9 Claims, 2 Drawing Sheets

BALL LOCK JOINT AND INTRODUCER FOR VASO-OCCLUSIVE MEMBER

FIELD OF THE INVENTION

This invention is a surgical instrument. It is specifically for controllable delivery of vaso-occlusive devices to a selected site within the vasculature or other lumen of a human body by the use of a catheter. In particular, the inventive device includes a holding member which is at least generally tubular and has an opening through the tubular wall. The vaso-occlusive device to be delivered has, on one end, a mating member which may be at least partially pressed into the opening in the wall of the holding member. The mating member attached to the vaso-occlusive member is held in the opening with an interference wire. The interference wire is axially movable within the holding member and has a diameter sufficient to hold the mating member within the wall opening. Upon proximal movement of the interference wire, the mating member becomes free to leave the holding member. The interference wire may be tapered or not. The vaso-occlusive member may be a helically wound coil or a braid or other appropriate form. The invention generically includes the so-made joint incorporating the components for delivering the vaso-occlusive device.

Field of the Invention

The treatment of a variety of vascular and other maladies throughout the body using catheters is increasingly more important form of therapy. Catheters have been used to place various treatment materials, devices, and drugs within arteries and veins in the human body. Examples of these devices and their use in such treatments is shown in U.S. Pat. Nos. 5,234,437 ("Detachable Pusher-Vaso-Occlusive Coil Assembly With Threaded Coupling"); 5,261,916 ("Detachable Pusher-Vaso-Occlusive Coil Assembly With Interlocking Ball and Keyway Coupling"); and 5,250,071 ("Detachable Embolic Coil Assembly Using Interlocking Clasp"). These show methods and devices for delivery of vaso-occlusive or embolic coils or wires within the human body to sites such as aneurysms or other vascular accidents, to occlude those sites. Coils such as are discussed in those documents (as well as in U.S. Pat. No. 4,994,069, to Ritchart, et al.), may be of regular (or helical) configuration or assume a random or other convoluted configuration at the chosen treatment site. The vaso-occlusive devices normally are of a radio-opaque, biocompatible material such as platinum, gold, and other noble metals, tungsten, or alloys of these metals. Although it is not theoretically necessary, in treating aneurysms, it is common to place a number of helical coils within the aneurysm. It is, of course, possible to occlude an aneurysm using but a single coil. Such coils occlude the site by acting as a situs for thrombus formation.

Vaso-occlusive coils have typically been placed at the desired site within the body using a catheter and a pusher. Such deployment takes place in the following manner. The site is first accessed by the catheter. In treating vascular conditions requiring occlusion, the sites may be accessed with flexible, small diameter catheters such as those shown in U.S. Pat. Nos. 4,739,768 (to Engelson) and 4,813,934 (to Sepetka et al.). The catheter may be guided to the site via the use of guide wires (see, U.S. Pat. No. 4,884,579) or by flow directed means such as balloons placed at the distal end of catheters. The use of a guide wire involves the placement of relatively long, torqueable wire sections within the catheter, which wire has a more flexible distal end section designed to be advanced across sharp bends and vessel junctions. The guide wire tip is normally visible using fluoroscopy and is an elegant way to allow a catheter to be manipulated through extremely tortuous vessels, even when such vessels are surrounded by soft tissue such as the liver or brain. Once the guidewire and its attendant catheter reach the site to be treated, the catheter lumen is cleared by removing the guidewire (if a guidewire has been used), and the vaso-occlusive device is placed into the open end of the catheter. The vaso-occlusive device is then advanced through the catheter using a pusher. Pushers are normally wires having distal ends that are adapted either to meet or to engage and push the coil through the catheter lumen as the pusher itself is advanced through the catheter. When the coil reaches the distal end of the catheter, it is deployed from the catheter using that pusher into the vascular or other site. Although this technique of discharging the vaso-occlusive device from the distal end of the catheter has a number of undesirable limitations, it has the benefit of low cost and provides a short delivery time for multiple coils.

Several techniques have been developed to enable more accurate placement of coils within a selected site. One such technique (U.S. Pat. Nos. 5,122,136 and 5,354,295 to Guglielmi, et al.) employs a vaso-occlusive device which is bonded by a metal-to-metal joint to the distal end of the pusher. The joint is made of a more base metal, as compared to the vaso-occlusive device, and may be severed using electrolysis. In any event, the coil-carrying pushers advance through the catheter to the selected site and a small electrical current is passed through the pusher-coil assembly. The current causes the noted joint to be eroded away, probably via electrolysis. The pusher and the catheter may then be retracted leaving the detached coil at an exact position within the vessel. Although the electrolytic release of the coil takes place in a fairly short period of time, it is not as rapid as is simple mechanical detachment.

Another technique for detaching an embolic coil is described in U.S. Pat. No. 5,261,916. A coil having an enlarged end portion is mated with a pusher having a keyway adapted to receive the enlarged portion of the coil in an interlocking relationship. This relationship is maintained by a coaxial member which covers both the pusher and the coil end. The coaxial member is movable by sliding that member axially. As the coil member is moved away from the junction where the coils member engages the keyway, the coil disengages and the pusher may then be removed from the body. This disengagement requires that the end of the coil be moved in a radially direction upon disengagement from the pusher.

Another device for placement of coils is shown in U.S. Pat. No. 5,234,47. This device includes a vaso-occlusive coil having a helical portion at one end and a pusher which is threaded to the inside of a helical coil by use a threaded section on the outside of the pusher. The device operates to release the coil by engaging the proximal end of the coil with a sleeve while the pusher is unthreaded. Once the pusher is free, the sleeve may be used to push the coil out into the treatment area.

U.S. Pat. No. 5,250,071 shows an embolic coil having engagable and interlocking ramps at the end of the coil and having a passageway through the axis of the coil and the ramps. The axial passageway serves as a path for a central wire which locks the various coils together or locks the coil with the guidewire. Again, the tip of the coil must undergo radial movement to disengage from its company pusher.

Still another method of placing an embolic coil is shown in U.S. Pat. No. 5,108,407. This patent shows the use of a device in which embolic coils are separated from the distal end of a pusher by the use of a heat releasable adhesive bond. The coil adheres to the pusher via a mounting connection using a heat sensitive adhesive. Laser energy is transferred through a fiber optic cable, which cable terminates at the adhesive bearing connector. As the connector becomes warm, the adhesive bond between the connector and coil releases.

None of the devices disclosed above suggests the use of an interference lock joint of the type which is described in more detail below.

SUMMARY OF THE INVENTION

This invention is an interference lock joint for holding and releasing a vaso-occlusive member. The vaso-occlusive member is designed to be placed within the vasculature (or other opening within a human body) so to occlude that site. The vaso-occlusive member may be a coil, or a braid, or other such known member. The vaso-occlusive member has in particular a mating portion which is fixedly attached to at least one end, preferably at its proximal end. The mating portion of the vaso-occlusive device is configured in such a way that it may be held within a tubular holding member. The tubular holding member has an opening through its wall. The interference wire is a wire, perhaps of constant diameter, perhaps with a taper, which extends from the holding member wall opening to the outside of the patient. When the interference wire is retracted from the vicinity of the wall opening, the mating region of the vaso-occlusive device is then free to move within the holding member. It is not ejected nor pushed from the distal end of the catheter as are many such designs. It is free to stay in a single location and the delivery apparatus removed from around it.

DESCRIPTION OF THE INVENTION

Figure 1:
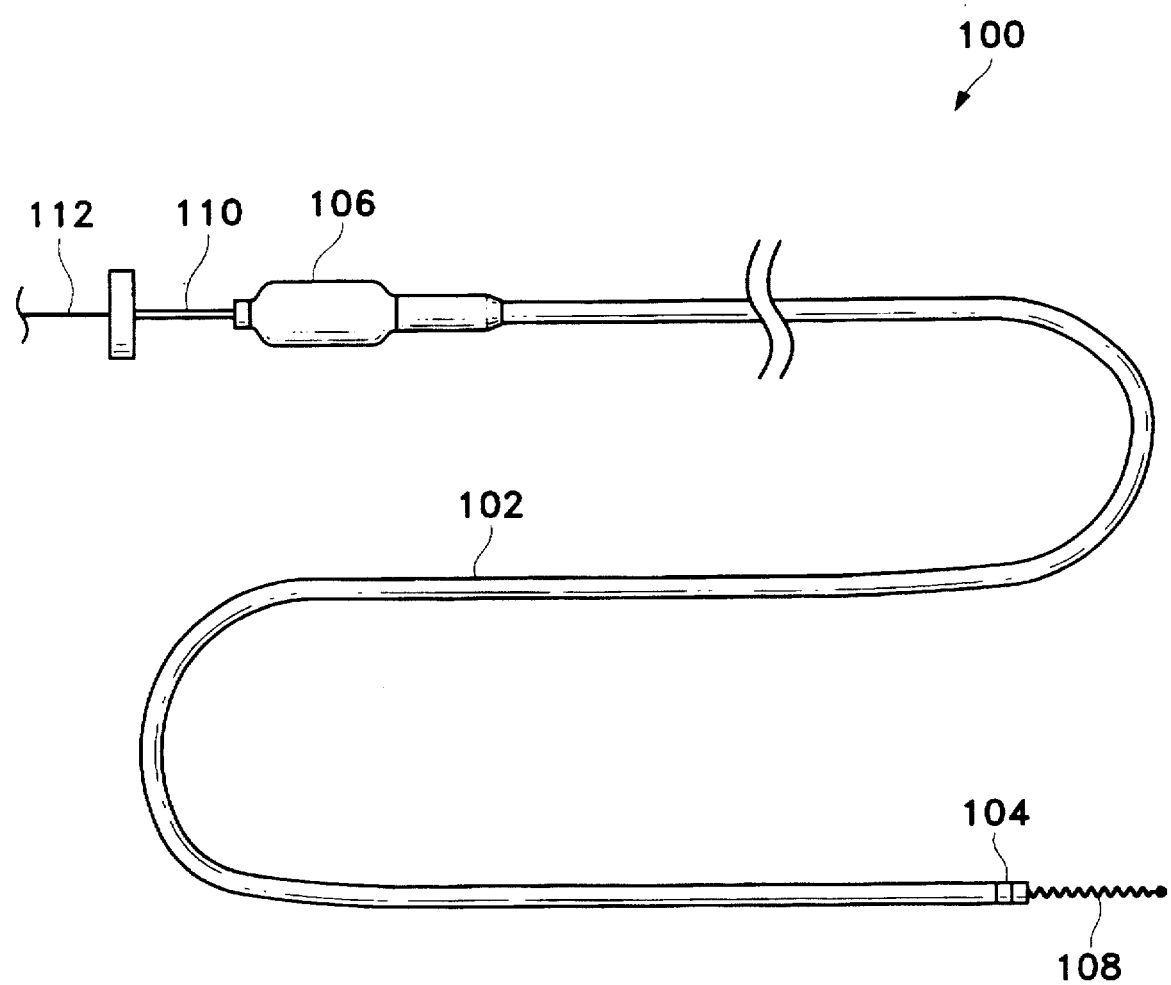
FIG. 1 shows a generic plan view of the system showing how the inventive joint and vaso-occlusive device are employed.

A catheter assembly (100) utilizing the invention is shown in FIG. 1. In particular, a tubular catheter (102) having a typical distal radio-opaque marker (104) and a proximal fitting (106) is shown. The details of catheter (102) form no particular aspect of the invention. Any catheter capable of delivering the inventive device to a chosen site is suitable in this assembly. Also shown in FIG. 1 is the vaso-occlusive device (108), shown to be a coil. The proximal-most end of the holding member (110) is also shown. Finally, interference wire (112) is shown extending proximally from assembly (100). It should be understood that the interference joint as it meets with the proximal end of vaso-occlusive device (108) may be situated anywhere within the inner lumen of catheter (102).

Figure 2:
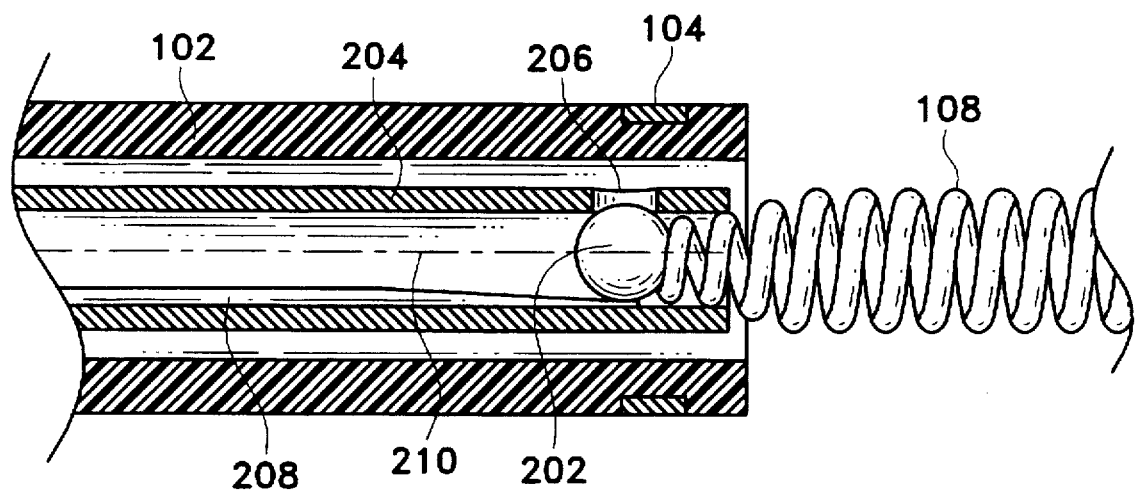
FIG. 2 shows in cross-section the distal tip of one variation of the joint made according to this invention.

FIG. 2 is a close-up, cross-section of the distal end of catheter (102). The optional radio-opaque banding (104) may be seen in cross-section. In particular, the vaso-occlusive device, again shown to be a helical coil (108), has a spherical member (202) on its distal end. Spherical member (202) is fixedly attached to vaso-occlusive member (108). In this variation, the diameter of vaso-occlusive member (108) is such that it will not proceed proximately within a holding member (204). Holding member (204) has a passageway or opening (206) through its wall. Holding member (204) is generally tubular and defines an open region in the vicinity of the opening (206). In this variation, the holding member (204) is produced from either a metallic or polymeric tubing which is of sufficient stiffness to maintain the position of the mating member (202) in place through the cooperation of interference wire (208). Holding member (204) may be made of a material such as a metallic hypotube, or polymeric materials such as polyimides (which are somewhat stiff) or even polymers or elastomers such as polyethylene or silicones if the mating member (202) will maintain its position with respect to holding member (204).

Figure 3:
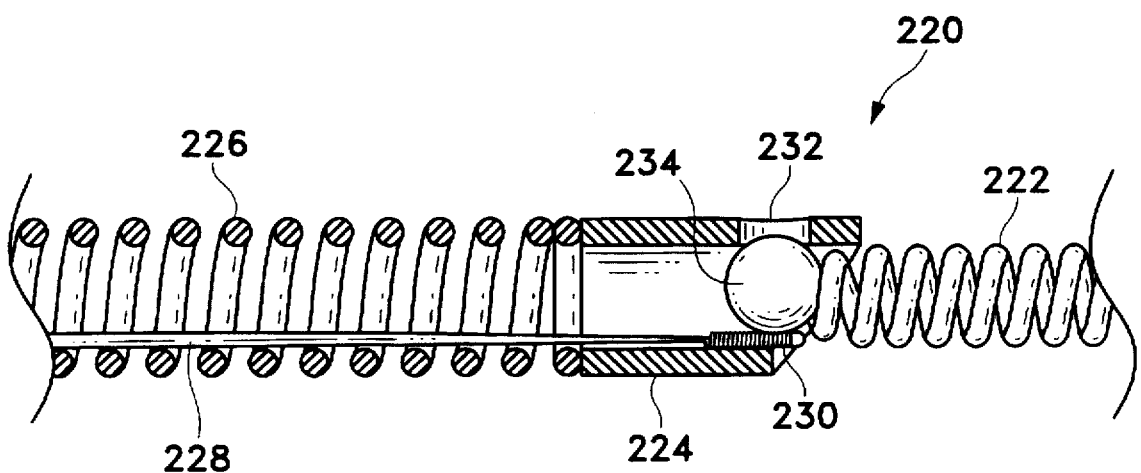
FIG. 3 shows another variation of an interlocking joint made according to this invention.

Holding member (204) is shown in FIG. 2 to extend proximally in catheter (102) in some unspecified way. It may extend to the proximal opening of catheter assembly (100) if the flexibility of the holding member is appropriate for the task involved or it may meet and join with another member which extends it use to the exterior of the catheter. As is shown in FIG. 3 below, the single function is to maintain the vaso-occlusive member (108) at a specific point so that it may be controllably deployed using interference wire (208). The details of the proximal construction of holding member (204) are not particularly critical.

Although the joint is shown to be within the interior of catheter (102), such, is obviously not necessary during deployment of the vaso-occlusive device (108). Although deployment of vaso-occlusive device (108) may take place with mating member (202) interior to catheter (102), such positioning is not the most desirable way of going about that deployment.

FIG. 3 shows in partial cross section, a variation (220) of the inventive joint (220). In this depiction, the catheter (102) found in FIGS. 1 and 2 is omitted for sake of clarity. This variation (220) shows a number of independent features which may be used as desired by a designer of a device made according to this invention. In particular, vaso-occlusive device (222) is of a diameter which is smaller than the outside diameter of holding member (224). The more proximal portion of holding member (224) is a coil (226). Furthermore, the control wire (228) is, within the visual portion shown in FIG. 3 a relatively constant diameter control wire (228) having on its distal tip, a small radio-opaque coil (230).

The variation (220) shown in FIG. 3 shows the flexibility of design of this inventive joint. The more distal region of holding member (224) may, as noted above, be metallic such as a hypotube, or may be a polymeric (soft, hard, or flexible) having an opening (232) therein. It operates in the same way as does the variation shown in FIG. 2. As was noted above, the more proximal portion of the holding member— whatever the variation—is simply to provide a firm control of a positioning relative to the interference wire (228) prior to the time that the vaso-occlusive device (222) is deployed. The proximal section of holding member (206) is therefore shown to be a coil and it may just as easily be a braid or wire or tubing or other variations as discussed above.

Vaso-occlusive device (222), again shown as a coil, has a smaller diameter than the vaso-occlusive device (108) shown in FIG. 2. This is simply to depict that the size of the vaso-occlusive device is not at all critical and may be of any convenient size or form in using this invention.

Finally, the interference wire (228) shown in this variation of the invention is constructed in a way which is quite similar to a guidewire used for placement for endovascular catheters. This is merely to show that the only critical limitation of the interference wire (228) is its ability to press the mating member (234) into opening (233). As noted above, conventional catheter insertion and navigational techniques involving guidewires or flow directed devices are used to place the distal end of a catheter at the chosen site. Once the distal end of the catheter is positioned at that site, the vaso-occlusive device (108 in FIG. 2 or 222 in FIG. 3) engaged within a holding member (204 in FIG. 2 or 226 in FIG. 3) is inserted and forwarded to the chosen site in the body. Obviously, the interference wire (208 in FIG. 2 or 228 in FIG. 3) is in such a position during this introductory step that the whole assembly may be forwarded through the catheter as an assembly. Once the site is achieved, the respective interference wire is removed and the catheter, holding member, and interference wire are each withdrawn from the body.

Modifications of the device described above in methods of using it and keeping with the invention that are apparent to those having ordinary skill in the mechanical or surgical instrument design art are intended to be within the scope of the claims which follow.

I claim as my invention:

1. An interference locking joint for releasably holding a vaso-occlusive member comprising:
   (a) a holding member comprising a tubular wall section defining an opening through said tubular wall section, said tubular wall section having a longitudinal axis, and defining an interior space,
   (b) a mating member fixedly attached to the vaso-occlusive member, said mating member further configured to at least partially enter said opening in cooperation with an interference wire, and upon entering said opening, prevent axial movement with relation to said holding member, said mating member being axially moveable within said holding member when said mating member is not cooperating with said interference wire and
   (c) said interference wire, axially moveable within said holding member and having a diameter suitable for causing said mating member to at least partially enter said holding member opening.

2. The interference locking joint of claim 1 wherein said vaso-occlusive member is a helical coil.

3. The interference locking joint of claim 2 wherein said helical coil is axially moveable through said holding member.

4. The interference locking joint of claim 2 wherein said helical coil is not axially moveable through said holding member.

5. The interference locking joint of claim 1 wherein the vaso-occlusive member is a braid.

6. The vaso-occlusive locking joint of claim 1 wherein the mating member is spherical.

7. The interference locking joint of claim 1 wherein the interference wire is tapered.

8. The interference locking joint of claim 1 wherein the interference wire has a constant diameter.

9. The interference locking joint of claim 1 further comprising a catheter coaxial with at least a portion of said holding member.

* * * * *